United States Patent
Kuo et al.

(10) Patent No.: US 7,439,361 B2
(45) Date of Patent: Oct. 21, 2008

(54) PROCESS FOR PREPARING SUBSTITUTED 5-AMINO-PYRAZOLO-[4,3-E]-1,2,4-TRIAZOLO[1,5-C]PYRIMIDINES

(75) Inventors: Shen-Chun Kuo, Union, NJ (US); David Jieh-Shyh Tsai, Warren, NJ (US); Loc Thanh Tran, Piscataway, NJ (US); Pengyi Zhang, Edison, NJ (US); Andrew D. Jones, Boston, MA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/788,682

(22) Filed: Apr. 20, 2007

(65) Prior Publication Data

US 2007/0203340 A1   Aug. 30, 2007

Related U.S. Application Data

(63) Continuation of application No. 10/973,631, filed on Oct. 26, 2004, now Pat. No. 7,223,861.

(60) Provisional application No. 60/515,051, filed on Oct. 28, 2003.

(51) Int. Cl.
*C07D 403/00* (2006.01)
(52) U.S. Cl. .................................................. 544/371
(58) Field of Classification Search ............... 544/371
See application file for complete search history.

(56) References Cited

U.S. PATENT DOCUMENTS 6,407,236 B1 * 6/2002 Baraldi et al. ............... 544/251

FOREIGN PATENT DOCUMENTS

| EP | 1 364 953 | 11/2003 |
| WO | WO 95/01356 | 1/1995 |
| WO | WO 01/92264 | 12/2001 |

OTHER PUBLICATIONS

Baraldi, et. al.; "Design, Synthesis and Biological Evaluation of $C^9$—and $C^2$-Substituted Pyrazolo [4,3-e]-1,2,4-triazolo [1,5-c] pyrimidines as New $A_2A$ and $A_3$ Adenosine Receptors Antagonists", *J. Med. Chem.*; 46 (2003); pp. 1229-1241.
Baraldi, et. et al.; "Design, Synthesis, and Biological Evaluation of a Second Generation of Pyrazolo [4,3-e]-1,2,4-triazolo [1,5-c] pyrimidines as Potent and Selective $A_{2A}$ Adenosine Receptor Antagonists", *J. Med. Chem.*; 41 (1998); pp. 2126-2133.
Baraldi, et. al.; "Pyrazolo [4,3-e]-1,2,4-triazolo [1,5-c] pyrimidine Derivatives: Potent and Selective $A_{2A}$ Adenosine Antagonists", *J. Med. Chem.*; 39 (1996); pp. 1164-1171.

* cited by examiner

*Primary Examiner*—James O. Wilson
*Assistant Examiner*—Erich A Leeser
(74) *Attorney, Agent, or Firm*—Patent Practitioners of Schering Corporation

(57) ABSTRACT

A process for preparing substituted 5-amino-pyrazolo[4,3-e]-1,2,4-triazolo-[1,5-c]pyrimidine compounds having an aminoalkyl substituent at the 7-position is disclosed, wherein the pyrimidine ring is cyclized using a cyanating agent.

1 Claim, No Drawings

PROCESS FOR PREPARING SUBSTITUTED 5-AMINO-PYRAZOLO-[4,3-E]-1,2,4-TRIAZOLO[1,5-C]PYRIMIDINES

CROSS REFERENCE TO RELATED APPLICATION

This application is a continuing application based on and claiming the priority of U.S. patent application Ser. No. 10/973,631 filed Oct. 26, 2004, which in turn claims the benefit of U.S. Provisional Application No. 60/515,051, filed Oct. 28, 2003, each of which is incorporated herein by reference in its entirety.

FIELD OF THE INVENTION

The present invention relates to a process for preparing substituted 5-amino-pyrazolo[4,3-e]-1,2,4-triazolo-[1,5-c]pyrimidine compounds having an aminoalkyl substituent at the 7-position.

BACKGROUND

Substituted 5-amino-pyrazolo[4,3-e]-1,2,4-triazolo-[1,5-c]pyrimidine compounds disclosed in WO 01/92264 are useful as $A_{2a}$ receptor antagonists in the treatment of central nervous system diseases, in particular Parkinson's disease.

WO 01/92264 discloses processes for preparing 5-amino-2substituted-pyrazolo[4,3-e]-1,2,4-triazolo-[1,5-c]pyrimidines comprising dehydrative rearrangement of hydrazines. Baraldi et al, *J. Med. Chem.*, 41, (1998), p. 2126-2133 disclose formation of a 5-amino-pyrazolo[4,3-e]-1,2,4-triazolo-[1,5-c]pyrimidine having a phenylalkyl substituent at the 7-position, wherein the reaction comprises reacting a phenylalkyl-substituted hydrazide with (ethoxymethylene)malonitrile to form a substituted pyrazole. Baraldi et al, *J. Med. Chem.*, 39, (1996), p. 1164-1171 disclose formation of a 7-substituted 5-amino-pyrazolo[4,3-e]-1,2,4-triazolo-[1,5-c]pyrimidine by reaction of an alkylated pyrazole with (ethoxymethylene)malonitrile. Both Baraldi et al process use $NH_2CN$ to accomplish the final ring closure.

SUMMARY OF THE INVENTION

The present invention relates to a process for preparing compounds having the structural formula I

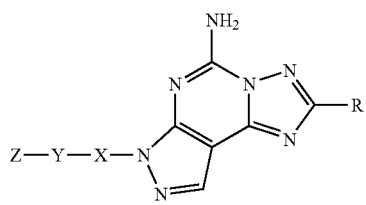

or a pharmaceutically acceptable salt or solvate thereof, wherein

R is $R^1$-furanyl, $R^1$-thienyl, $R^1$-pyridyl, $R^1$-pyridyl N-oxide, $R^1$-oxazolyl, $R^{10}$-phenyl, $R^1$-pyrrolyl or cycloalkenyl;

X is $C_2$-$C_6$ alkylene;

Y is —N($R^2$)$CH_2CH_2$N($R^3$)—, —OCH$_2$CH$_2$N($R^2$)—, —(CH$_2$)$_2$—NH—, or

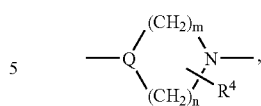

and

Z is $R^5$-phenyl, $R^5$-phenylalkyl, $R^5$-heteroaryl, diphenylmethyl, $R^6$—C(O)—, $R^6$SO$_2$—,

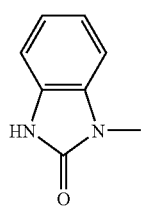

or phenyl-CH(OH)—; or when Q is

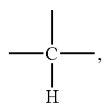

Z is also phenylamino or pyridylamino;

or

Z and Y together are

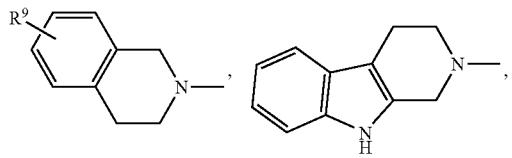

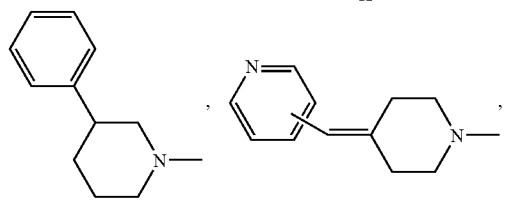

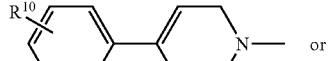

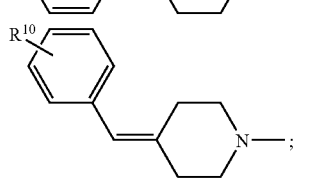

$R^1$ is 1 to 3 substituents independently selected from hydrogen, alkyl, —CF$_3$, halogen, —NO$_2$, —NR$^{12}$R$^3$, alkoxy, alkylthio, alkylsulfinyl, and alkylsulfonyl;

$R^2$ and $R^3$ are independently selected from the group consisting of hydrogen and alkyl;
m and n are independently 2-3;
Q is

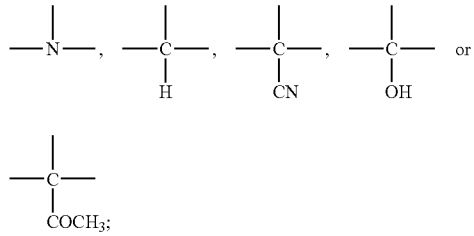

$R^4$ is 1-2 substituents independently selected from the group consisting of hydrogen and alkyl, or two $R^4$ substituents on the same carbon can form =O;

$R^5$ is 1 to 5 substituents independently selected from the group consisting of hydrogen, halogen, alkyl, hydroxy, alkoxy, —CN, dialkyl-amino, —$CF_3$, —$OCF_3$, acetyl, —$NO_2$, hydroxyalkoxy, alkoxyalkoxy, dialkoxy-alkoxy, alkoxy-alkoxy-alkoxy, carboxy-alkoxy, alkoxycarbonylalkoxy, cycloalkyl-alkoxy, dialkyl-amino-alkoxy, morpholinyl, alkyl-$SO_2$—, alkyl-$SO_2$-alkoxy, tetrahydropyranyloxy, alkylcarbonyl-alkoxy, alkoxycarbonyl, alkylcarbonyloxy-alkoxy, —$SO_2NH_2$, or phenoxy; or adjacent $R^5$ substituents together are —O—$CH_2$—O—, —O—$CH_2CH_2$—O—, —O—$CF_2$—O— or —O—$CF_2CF_2$—O— and form a ring with the carbon atoms to which they are attached;

$R^6$ is alkyl, $R^5$-phenyl, $R^5$-phenylalkyl, thienyl, pyridyl, cycloalkyl, alkyl-OC(O)—NH—($C_1$-$C_6$)alkyl-, dialkyl-aminomethyl, or

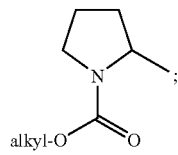

$R^9$ is 1-2 groups independently selected from hydrogen, alkyl, hydroxy, alkoxy, halogen, —$CF_3$ and alkoxy-alkoxy;

$R^{10}$ is 1 to 5 substituents independently selected from the group consisting of hydrogen, halogen, alkyl, hydroxy, alkoxy, —CN, —$NH_2$, alkylamino, dialkylamino, —$CF_3$, —$OCF_3$ and —$S(O)_{0-2}$alkyl;

$R^{12}$ is H or alkyl; and $R^{13}$ is alkyl-C(O)— or alkyl-$SO_2$—; comprising a) reacting the hydroxyl group of a pyrazole of formula II

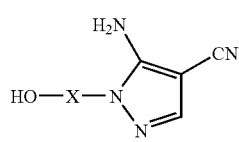

with an activating agent in the presence of a base to obtain a compound of formula III

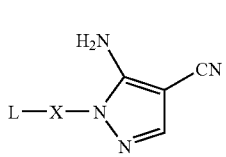

wherein L is a leaving group,
and coupling the compound of formula III with a compound of formula IV

Z—Y—H                                         IV in the presence of a base to obtain a compound of formula V

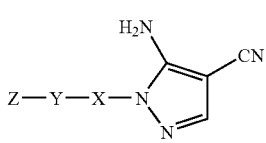

b) treating the compound of formula V with trialkyl orthoformate in the presence of a catalytic amount of acid to obtain a compound of formula VI

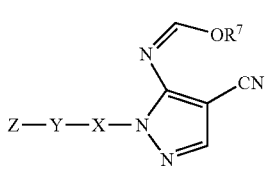

wherein $R^7$ is alkyl;

c) condensing the compound of formula VI with a hydrazide of formula VII $H_2$NHN—C(O)—R                                VII in the presence of an acid to obtain a compound of formula VIII

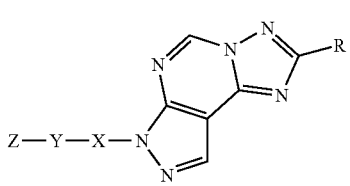

and hydrolyzing the compound of formula VIII to obtain a compound of formula IX

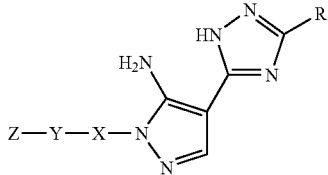

d) cyclizing the compound of formula IX with a cyanating agent selected from the group consisting of cyanates and cyanogen halides in the presence of a base to obtain a compound of formula I.

In particular, the invention relates to cyclizing a compound of formula IX with a cyanating agent to obtain a compound of formula I.

DETAILED DESCRIPTION

Preferred compounds of formula I prepared by the claimed process are those wherein R is $R^1$-furanyl, $R^1$-thienyl, $R^1$-pyrrolyl or $R^{10}$-phenyl, more preferably $R^1$-furanyl. $R^1$ is preferably hydrogen or halogen.

Another group of preferred compounds is that wherein X is ethylene.

Y is preferably

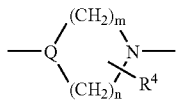

wherein Q is

with Q preferably being nitrogen. Preferably, m and n are each 2, and $R^4$ is H.

A preferred definition for Z is $R^5$-phenyl, $R^5$-heteroaryl, $R^6$—C(O)— or $R^6$—SO$_2$—. $R^5$ is preferably H, halogen, alkyl, alkoxy, hydroxyalkoxy or alkoxyalkoxy. $R^6$ is preferably $R^5$-phenyl. Especially preferred are compounds wherein Z is $R^5$-phenyl and $R^5$ is one substituent selected from the group consisting of alkoxy and alkoxyalkoxy. A preferred alkoxy group is methoxy, with alkoxyalkoxy being more preferred, e.g., methoxyethoxy and ethoxyethoxy; methoxyethoxy is most preferred.

In step a, preferred embodiments of the process use a compound of formula IV-A:

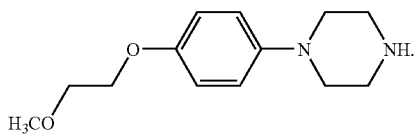

In step b, the preferred trialkyl orthoformate is triethyl orthoformate.

Preferred embodiments of the process use 2-furoic hydrazide in step c (formula VII), thus preparing compounds of formula I wherein R is 2-furyl.

Preferred reagents for the cyclization in step f are cyanates.

In a preferred aspect, the process of the invention comprises the preparation of compounds of the formulas I-A to I-C:

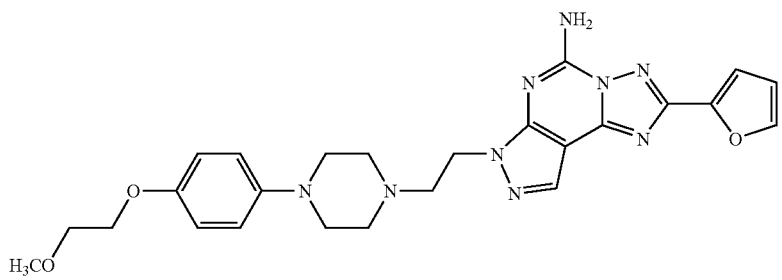

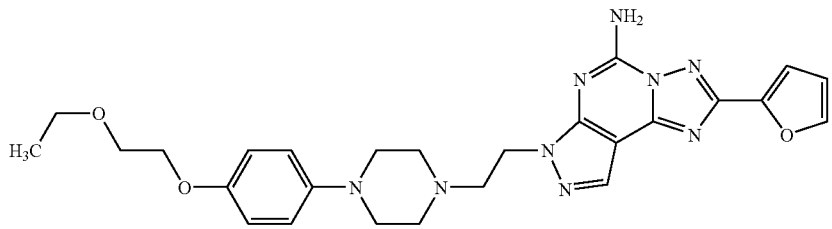

-continued

I-C

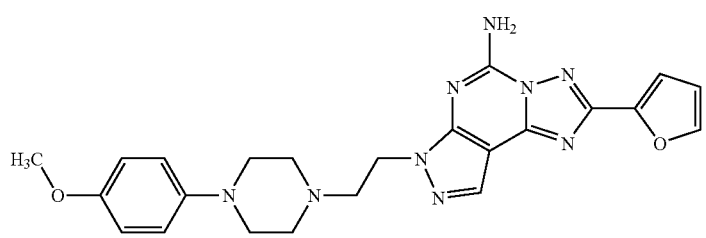

In a most preferred aspect, the process of the invention comprises the preparation of a compound of formula I-A comprising:

a) reacting the hydroxyl group of a pyrazole of formula II

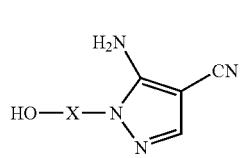
II with methanesulfonyl chloride in the presence of a base to obtain a compound of formula IIIa

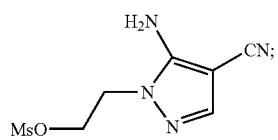
IIIa and coupling the compound of formula IIIa with a compound of formula IVa

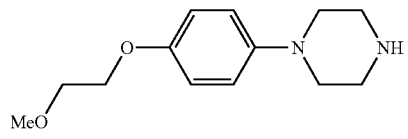
IVa in the presence of a base to obtain a compound of formula Va

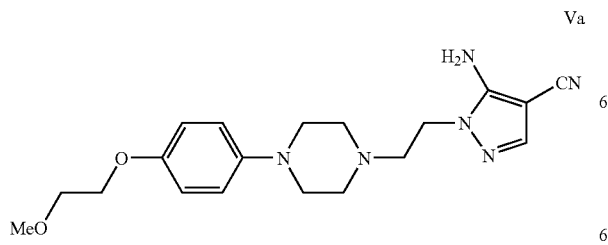
Va b) treating the compound of formula Va with trimethyl orthoformate in the presence of a catalytic amount of an acid to obtain a compound of formula VIa

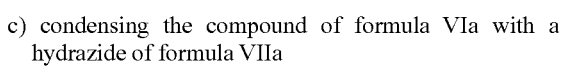
VIa c) condensing the compound of formula VIa with a hydrazide of formula VIIa

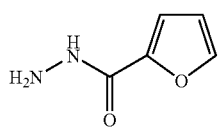
VIIa in the presence of an acid to obtain a compound of formula VIIIa

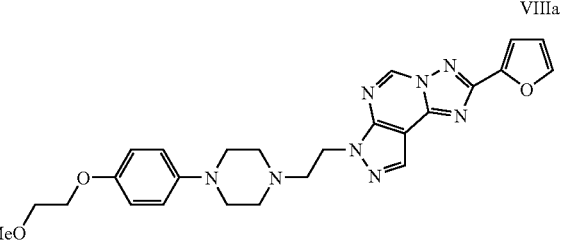
VIIIa and hydrolyzing the compound of formula VIIIa to obtain a compound of formula IXa

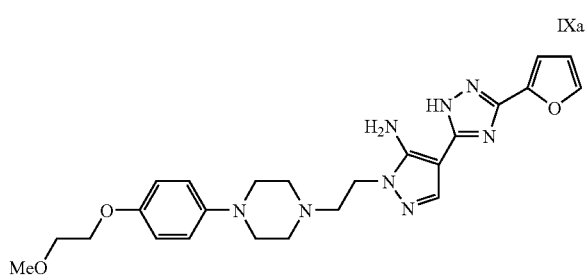

IXa d) cyclizing the compound of formula IXa with a cyanating agent selected from the group consisting of cyanates and cyanogen halides in the presence of a base.

Starting materials of formula II are known in the art (see, for example, Baraldi et al, *J. Med. Chem.*, 39, (1996), p 1165).

In step a, the hydroxyl group on the compound of formula II is reacted with an activating agent comprising a leaving group, L, wherein L is an optionally substituted alkylsulfonyl- or arylsulfonyl- group. When L is a sulfonyl group such as methanesulfonyl, trifluoromethanesulfonyll, ethanesulfonyl, benzenesulfonyl, p-toluenesulfonyl, p-bromobenzenesulfonyl or m-nitrobenzene-sulfonyl, typically the L-containing activating agent is an L-halide, e.g., methansulfonyl chloride. A preferred leaving group is methanesulfonyl.

The reaction is carried out in a non-protic organic solvent such as $CH_3CN$ at a temperature of about −20° C. to about 0° C., most preferably at about 0° C. About 1-2, preferably about 1-1.5 equivalents of activating reagent are used, and about 1-2, preferably about 1-1.5 equivalents of an organic base such as diisopropylethyl amine. The activated compound of formula III is not isolated.

The compound of formula III is coupled with an amine of formula IV. The reaction is carried out in the presence of an inorganic base such as NaOH or $K_2CO_3$, at a temperature range of −50° C. to about 150° C., preferably at about −20° C. to about 0° C., most preferably at about −10° C. About 1-2 equivalents of base are used.

In step b, the amino substituent on the compound of formula V is converted to the imidate by treatment with 1-10 equivalents of a trialkyl orthoformate in a non-protic organic solvent such as toluene at reflux temperature in the presence of a catalytic amount of acid (e.g., about 1 mol %). Any organic or inorganic acid can be used, but a preferred acid is p-tolunensulfonic acid. A preferred trialkyl orthoformate is trimethyl orthoformate.

The imidate of formula VI is then condensed with a hydrazide of formula VII in step c. The reaction is carried out in an organic solvent such as toluene at a temperature range of about −20° C. to about 110° C. in the presence of 1-2 equivalents of an acid such as isobutyric acid.

The compound of formula VIII is then hydrolysed under acidic conditions to form the ring-opened compound of formula IX. The acid can be a mineral acid or an alkyl or aryl sulfonic acid; the concentration of acid is not critical, but is preferably at 2-5%. The reaction is carried out at temperature range of about room temperature to about 110° C.

In step d, the compound of formula IX is cyclized by treatment with a cyanating agent selected from the group consisting of cyanates and cyanogen halides to obtain a compound of formula I. The reaction is conducted in an organic solvent such as $CH_3CN$ or tetrahydrofuran (THF) at a ratio of 4-20 w/v, preferably about 5 w/v, optionally in the presence of water (0 to 30% v/v, preferably about 10%). An inorganic base (e.g., $Na_2CO_3$, $NaHCO_3$, $KHCO_3$, NaOH, KOH, $K_3PO_4$, $K_2HPO_4$, $Na_3PO_4$, $Na_2HPO_4$) or organic base (e.g., trialkylamine) is added a ratio of about 0.2 to 0.5 equivalents. The reaction is carried out at a temperature of about 35° C. to reflux, preferably about 53° C. to about 58° C. 1-2 equivalents of the cyanating agent are used, wherein the cyanating agent is a cyanate or a cyanogen halide. Cyanates (i.e., compounds of the formula Ar—OCN, wherein Ar is an optionally substituted aromatic moiety) are exemplified by substituted phenyl cyanates such as 2-methoxyphenyl cyanate, 4-methoxyphenyl cyanate, 4-phenylphenyl cyanate and bisphenol A cyanate. Cyanogen halides are exemplified by cyanogen bromide and cyanogen chloride. Cyanates are preferred, with 2-methoxyphenyl cyanate being most preferred. The reaction is quenched by the addition of an aqueous solution of an inorganic base (e.g., $Na_2CO_3$, $NaHCO_3$, $KHCO_3$, NaOH, KOH, $K_3PO_4$, $K_2HPO_4$, $Na_3PO_4$, $Na_2HPO_4$).

The present process provides an advantage over the procedures previously reported in the art. Known processes used highly toxic and corrosive $NH_2CN$ to cyclize the ring, while the present process uses a cyanating agent such as a cyanate (e.g., 2-methoxyphenyl cyanate) or a cyanogen halide (e.g., cyanogen bromide). Furthermore, the preferred cyanating agents, cyanates, are preferable to the relatively more toxic cyanogen halides. Also, the temperature range for conducting the second part of step a of this invention is about 150° C. lower than that used in literature preparations. The present invention therefore, allows for large scale production and high yields using milder conditions.

As used herein, "alkyl" means an aliphatic hydrocarbon group which may be straight or branched and comprising about 1 to about 6 carbon atoms in the chain. Branched means that one or more lower alkyl groups such as methyl, ethyl or propyl, are attached to a linear alkyl chain. Alkylene, referring to a divalent alkyl group, similarly refers to straight or branched chains.

"Alkoxy" means an alkyl-O— group in which the alkyl group is as previously described, unless otherwise noted. Non-limiting examples of suitable alkoxy groups include methoxy, ethoxy, n-propoxy, isopropoxy, n-butoxy and heptoxy. The bond to the parent moiety is through the ether oxygen.

"Cycloalkyl" means a non-aromatic ring system comprising about 3 to about 6 carbon atoms. Non-limiting examples of suitable monocyclic cycloalkyls include cyclopropyl, cyclopentyl and cyclohexyl, and the like. Cycloalkylene refers to a divalent cycloalkyl group. Cycloalkenyl refers to a $C_4$-$C_6$ cycloalkyl ring comprising one double bond.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl.

R[5]-substituted heteroaryl refers to such groups wherein substitutable ring carbon atoms have a substituent as defined above.

"Alkylthio" means an alkyl-S— group in which the alkyl group is as previously described. Non-limiting examples of suitable alkylthio groups include methylthio, ethylthio, and i-propylthio. The bond to the parent moiety is through the sulfur.

"Alkylsulfonyl" means an alkyl-S(O$_2$)— group. The bond to the parent moiety is through the sulfonyl.

"Alkylsulfinyl" means an alkyl-S(O)— group. The bond to the parent moiety is through the sulfinyl.

"Carbonyl" means a —C(O)— moiety, e.g., alkoxycarbonyl refers to an alkoxy-C(O)— group (i.e., alkyl-O—C(O)—).

"Acetyl" means —C(O)CH$_3$.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Following are descriptions of the preparation of compound I-A using the claimed process.

The following abbreviations are used in the specification and claims: Ms (methylsulfonyl); Me (methyl); Et (ethyl); LOD (loss on drying); DMAP (4-dimethylamino-pyridine); and DMSO (dimethyl sulfoxide).

EXAMPLE 1

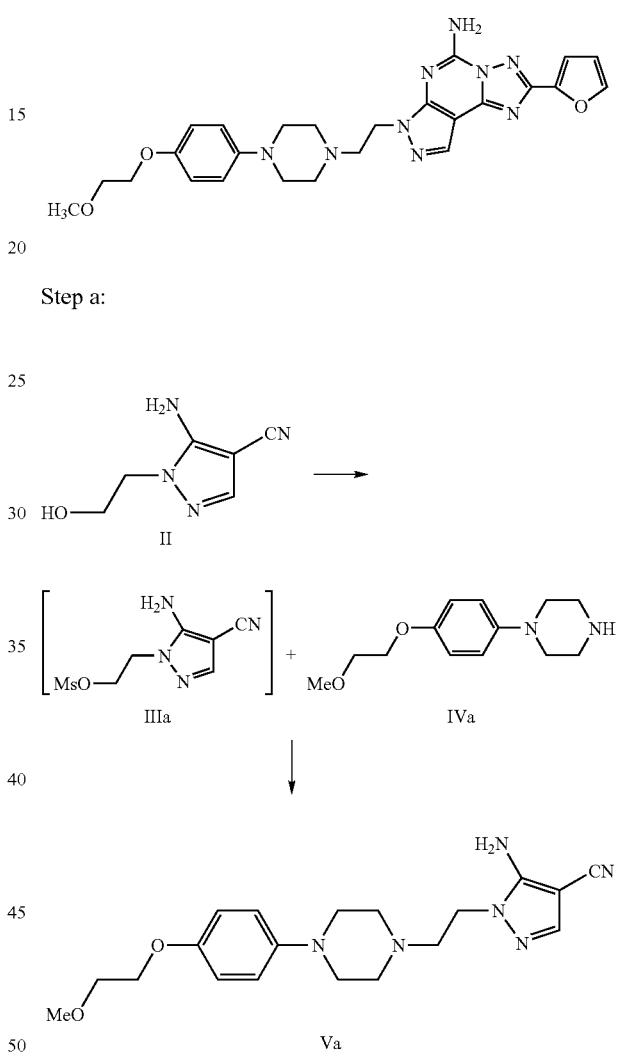

Step a:

To a mixture of compound II (200.0 g, 1.0 eq.) and diisopropylethyl amine (280 ml, 1.2 eq.) in CH$_3$CN (600 ml) at 0° C. was slowly added CH$_3$SO$_2$Cl (112 ml, 1.1 eq.). After the addition was complete, NaOH (25%, 250 ml) was added at 5° C. followed by a solution of compound IVa (34.2 g, 1.1 eq.) in water (600 ml). The reaction mixture was refluxed for 6 h, and then concentrated to a volume of 900 ml to remove CH$_3$CN. Water (1.2 l) was added to the reaction mixture and the batch was cooled to 22° C. The batch was filtered and washed the wet cake with water (600 ml), and dried in a vacuum at 65° C. for 24 h. A yellow product was obtained (ca. 415 g).

$^1$H NMR (CDCl$_3$): 7.52 (s, 1H), 6.95 (s, 4H), 5.89 (s, 2H), 4.18 (m, 2H), 4.06 (m, 2H), 3.78 (m, 2H), 3.47 (s, 3H), 3.11 (m, 4H), 2.83 (m, 2H), 2.72 (m, 4H).

Step b:

Va ⟶

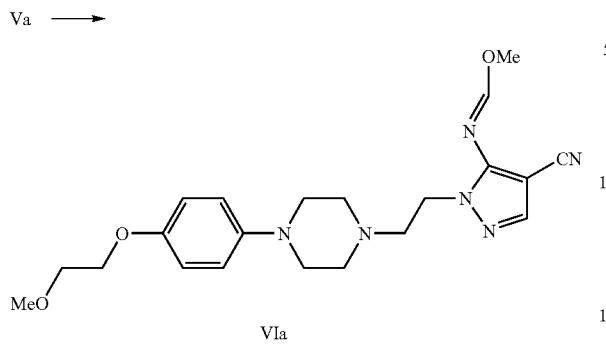

VIa

A mixture of compound Va (150.0 g, 1.0 eq.), trimethyl orthoformate (120 ml, 2.6 eq.) and a catalytic amount of p-toluenesulfonic acid in toluene (1.2 l) was heated to a temperature between 105 and 115° C. The reaction mixture was slowly concentrated to 520 ml. The reaction mixture was then cooled to 15 to 25° C. and heptane (1.6 l) was added to complete the precipitation. The batch was filtered, washed with heptane and dried in a vacuum oven at 20 to 30° C. for about 24 h to a LOD<0.5%. A light gray product was obtained (ca. 160.8 g).

Mass spectrum: M+1=413. $^1$H NMR (DMSO): 8.55 (s, 1H), 7.90 (s, 1H), 6.80 (m, 4H), 4.15 (m, 2H), 4.00 (m, 2H), 3.95 (s, 3H), 3.65 (m, 2H), 3.30 (s, 3H), 2.94 (bs, 4H), 2.70 (bs, 2H), 2.55 (bs, 4H). $^{13}$C NMR (DMSO): 162.5, 152.4, 150.4, 141.4, 117.6, 115.3, 114.8, 79.7, 70.9, 67.5, 58.5, 56.9, 55.0, 53.0, 49.7, 45.3.

Alternate Step b:

Va ⟶

VIb

A mixture of compound Va (300.0 g, 1.0 eq.), triethyl orthoformate (280 ml, 2.6 eq.) and a catalytic amount of p-toluenesulfonic acid (3.0 g) in toluene (1.8 l) was heated to a temperature between 105 and 115° C. The reaction mixture was slowly concentrated to 1000 ml. The reaction mixture was then cooled to 15 to 25° C. and heptane (2.1 l) was added to complete the precipitation. The batch was filtered, washed with heptane and dried in a vacuum oven at 20 to 30° C. for about 24 h to a LOD<0.5%. A light gray product, VIb, was obtained (ca. 301.2 g).

Mass Spectrum: M+1=427. $^1$H NMR (DMSO): 8.50 (S, 1H), 7.92 (S, 1H), 6.81 (m, 4H), 4.35 (m, 2H), 4.10 (t, 2H), 3.99 (m 2H), 3.60 (m, 2H), 3.30 (s, 3H), 2.90 (bs, 4H), 2.50 (m, 4H), 2.70 (t, 2H), 1.38 (t, 3H). $^{13}$C NMR (DMSO): 162.1, 152.4, 150.6, 145.8, 141.4, 117.6, 115.3, 114.9, 79.7, 70.9, 67.4, 64.1, 58.5, 56.9, 53.0, 49.7, 45.4, 14.2.

Steps c:

VIa + H$_2$N-NH-C(O)-furan   → (1. Isobutyric acid, Toluene, 50° C.; 2. 110° C.)

VIIa

VIIIa

↓

IXa •HCl

Compound VIa (100 g, 1.0 eq.), compound VIIa (2-furoic hydrazide) (28.8 g, 0.97 eq.), toluene (400 ml), and isobutyric acid (23 ml, 1.0 eq.) were combined and the reaction mixture was heated to 50° C. and stirred for over 4 h. The reaction mixture was distilled off to about 300 ml at 50° C. The reaction mixture was heated to 110° C., azeotropic distillation was done to remove the water generated during the reaction, and then the mixture was stirred at 110-115° C. for over 4 h. After cooling to 25° C., the reaction mixture was added to 4.1% HCl solution (450 ml) and heated to reflux. The reaction mixture was stirred at reflux for over 2 h, and then cooled to 25° C. The reaction mixture was settled and the aqueous layer was separated from the organic layer. The aqueous layer was heated to 50° C. and the pH adjusted to between 1.8 and 2.8. After pH adjustment, the aqueous layer was stirred at 50° C. for 30 min, and then slowly cooled to 0° C. for over 2 h. The aqueous layer was stirred at 0° C. for 1 h to complete the precipitation. The solid was filtered and washed with water (250 ml). The product was dried in a vacuum oven at 75-80° C. The product was isolated as a mono-HCl salt and the yield was 110 g (82%).

MS: m/z 479, 463, 447, 433, 419, 298, 286, 285, 272, 263, 249, 247, 243, 235, 229, 216, 206, 194, 191. $^1$H NMR (DMSO-d$_6$): δ 8.03 (s, 1H); 7.9 (d, 1H); 7.35 (d, 1H); 7.1 (m, 2H); 6.9 (m, 2H); 6.7 (m, 1H); 4.6 (m, 2H); 4.05 (m, 2H); 3.6 (m, 4H); 3.5 (broad, 6H); 3.3 (s, 3H); 2.5 (m, 2H).

Alternatively, an equivalent amount of compound VIb can be substituted for compound VIa to obtain compound IXa.

Step d:

To a mixture of compound IXa (100.0 g, 1.0 eq.) and KHCO$_3$ (40 g, 1.5 eq.) in CH$_3$CN (500 ml) and water (10 ml) at a temperature between 53 and 58° C. was slowly added 2-methoxyphenol cyanate (39.0 g, 1.35 eq.). The reaction mixture was agitated at a temperature between 53 and 58° C. for 1 h. Upon completion of the reaction, a 10% NaOH aqueous solution (200 ml) was added to quench the reaction.

The batch was then cooled to a temperature between 20 and 25° C., and filtered. The cake was washed with water (400 ml) and CN₃CN (400 ml) and dried in a vacuum oven at 65 to 75° C. for about 12 h. A white product was obtained (ca. 91.0 g) with about 95% yield.

Mass spectrum: M+1=504. $^1$H NMR (DMSO): 8.37 (s, 1H), 8.13 (bs, 2H), 7.95 (m, 1H), 7.18 (m, 1H), 6.78 (m, 4H), 6.70 (m, 1H), 4.38 (m, 2H), 4.93(m, 2H), 3.56 (m, 2H), 3.37 (s, 3H), 2.90 (m, 4H), 2.80 (m, 2H), 2.55 (m, 4H), 2.45 (m, 2H).

EXAMPLE 2

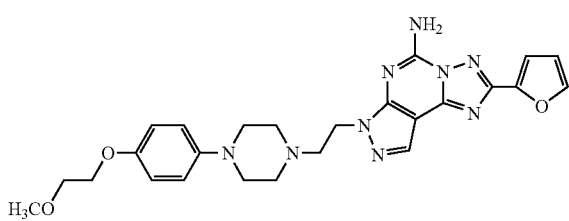

To a mixture of compound IXa (Example 1, step c) (50.0 g, 1.0 eq.) and DMAP (24.0 g, 2.0 eq.) in CH₃CN (850 ml) at a temperature between 75 and 85° C. was slowly added a solution of BrCN (15.0 g, 1.3 eq.) in CH₃CN (150.0 ml). The reaction mixture was refluxed for another 3 h. The reaction was cooled to 25° C., and 10% NaOH solution (500 ml) was added to quench the reaction. The batch was filtered, washed with water and dried in a vacuum oven at 65 to 75° C. for about 24 h. A light gray product was obtained (ca. 32.0g).

Mass spectrum: M+1=504. $^1$H NMR (DMSO): 8.37 (s, 1H), 8.13 (bs, 2H), 7.95 (m, 1H), 7.18 (m, 1H), 6.78 (m, 4H), 6.70 (m, 1H), 4.38 (m, 2H), 4.93(m, 2H), 3.56 (m, 2H), 3.37 (s, 3H), 2.90 (m, 4H), 2.80 (m, 2H), 2.55 (m, 4H), 2.45 (m, 2H).

EXAMPLE 3

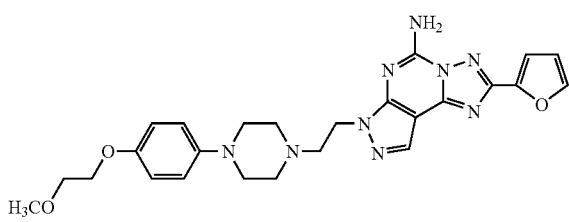

To a mixture of compound IXa (Example 1, step c) (100.0 g, 1.0 eq.) in THF (500 ml), water (100 ml) and NaOH (50%, 17.0 g) at a temperature between 60 and 70° C. was slowly added a solution of bisphenol-A cyanate (30.0 g, 1.1 eq.) in THF (125.0 ml). The reaction mixture was refluxed for another 1.5 h. The reaction mixture was cooled to 25° C., filtered, washed with water and dried in a vacuum oven at 65 to 75° C. for about 24 h. A light gray product was obtained (ca. 88.0 g).

Mass spectrum: M+1=504. $^1$H NMR (DMSO): 8.37 (s, 1H), 8.13 (bs, 2H), 7.95 (m, 1H), 7.18 (m, 1H), 6.78 (m, 4H), 6.70 (m, 1H), 4.38 (m, 2H), 4.93(m, 2H), 3.56 (m, 2H), 3.37 (s, 3H), 2.90 (m, 4H), 2.80 (m, 2H), 2.55 (m, 4H), 2.45 (m, 2H).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound selected from the following compounds:

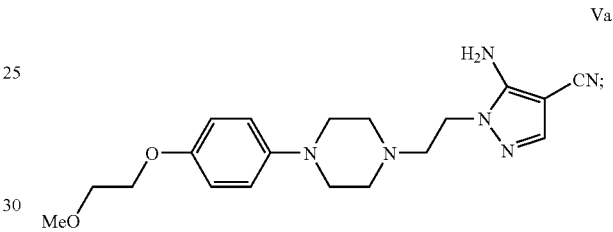

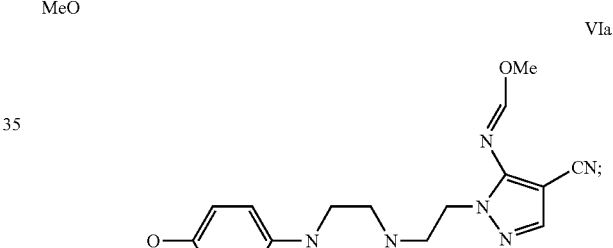

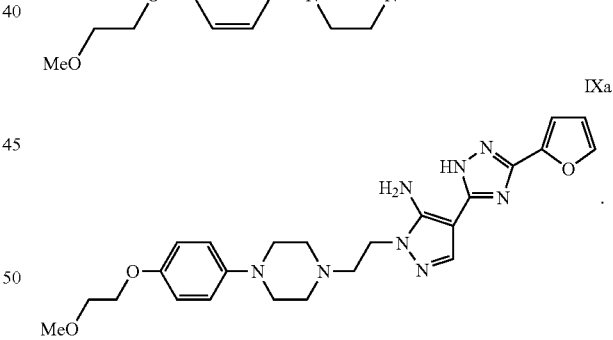

* * * * *